United States Patent
Mizumoto et al.

(10) Patent No.: US 8,986,328 B2
(45) Date of Patent: Mar. 24, 2015

(54) MEDICAL GRIPPING DEVICE

(75) Inventors: Yoshinori Mizumoto, Kyoto (JP); Tsuyoshi Nakakubo, Kyoto (JP)

(73) Assignee: Piolax Medical Devices, Inc., Yokohama-Shi, Kanagawa (JP)

( * ) Notice: Subject to any disclaimer, the term of this patent is extended or adjusted under 35 U.S.C. 154(b) by 967 days.

(21) Appl. No.: 12/998,752

(22) PCT Filed: Nov. 18, 2009

(86) PCT No.: PCT/JP2009/069899
§ 371 (c)(1),
(2), (4) Date: Aug. 15, 2011

(87) PCT Pub. No.: WO2010/061867
PCT Pub. Date: Jun. 3, 2010

(65) Prior Publication Data
US 2011/0295281 A1   Dec. 1, 2011

(30) Foreign Application Priority Data
Nov. 28, 2008   (JP) .................................. 2008-305096

(51) Int. Cl.
*A61B 17/00* (2006.01)
*A61B 17/08* (2006.01)
*A61B 17/10* (2006.01)

(52) U.S. Cl.
CPC ................. *A61B 17/10* (2013.01); *A61B 17/08* (2013.01); *A61B 17/083* (2013.01)
USPC ........... 606/151; 606/139; 606/142; 606/143; 606/150; 606/157; 606/170; 606/200; 606/205; 606/207; 606/208; 606/210; 604/19; 604/194

(58) Field of Classification Search
USPC ......... 606/139, 142, 143, 150, 151, 157, 200, 606/205, 207
See application file for complete search history.

(56) References Cited

U.S. PATENT DOCUMENTS 4,448,193 A * 5/1984 Ivanov ......................... 606/143
4,950,281 A   8/1990 Kirsch et al.

FOREIGN PATENT DOCUMENTS

| CN | 1046844 A | 11/1990 |
|---|---|---|
| DE | 1110359 B | 7/1961 |
| JP | 3068178 B2 | 7/2000 |
| JP | 2002-034998 A | 2/2002 |
| JP | 2005-013540 A | 1/2005 |
| WO | WO 91/13590 | 9/1991 |

OTHER PUBLICATIONS

Chinese Office Action dated Mar. 13, 2013 with English translation thereof.

* cited by examiner

*Primary Examiner* — Vy Q Bui
(74) *Attorney, Agent, or Firm* — McGinn IP Law Group, PLLC

(57) ABSTRACT

In a background-art medical gripping device, when a wall surface of an in vivo tissue has a large tear, a side portion of the tear can be gripped by the gripping device, but the other side portion opposed to the side portion cannot be gripped simultaneously. Therefore, to close the tear, complicated operation is required to be performed using plural gripping devices. A medical gripping device according to the present invention includes a fixed clip, a pair of movable clips made from an elastic material and provided to face the fixed clip, the movable clips having lower ends fixed to the fixed clip and the other ends opened, and a control mechanism which shifts from each other a timing at which a gripping target is gripped between one of the movable clips and the fixed clip and a timing at which the target is gripped between the other movable clip and the fixed clip.

14 Claims, 10 Drawing Sheets

MEDICAL GRIPPING DEVICE

TECHNICAL FIELD

The present invention relates to a medical gripping device for gripping an in vivo tissue such as a mucosa.

BACKGROUND ART

Various medical gripping devices for gripping in vivo tissues have been known. For example, Patent Document 1 discloses such a medical gripping device.

The example will be described roughly. Gripping forceps are designed to open/close through the remote control from a proximal side of a flexible sheathe. A clip gripping an in vivo tissue is engaged with the gripping forceps. When the gripping forceps are retracted into the sheathe, the clip is closed by a closing member. Thus, the in vivo tissue of a body is gripped by the clip. Then, the clip is prevented from opening.

Next, by operating the proximal side of the sheathe such that the gripping forceps come out from a distal end of the sheathe, the griping forceps are opened to be released from the engagement with the clip. Thus, the clip is left in the body while the other portions are extracted outside the body. In this manner, in vivo blood stanching, ligation, marking, or the like, can be carried out by the clip.

PRIOR TECHNICAL DOCUMENT

Patent Document

Patent Document 1: JP-2005-013540-A

SUMMARY OF THE INVENTION

Problems that the Invention is to Solve

According to such a medical gripping device, when a wall surface of an in vivo tissue has a large tear, while one side portion of the tear can be gripped, the other side portion opposed thereto cannot be gripped simultaneously. In order to close such the tear, a complicated operation using plural gripping devices is necessary.

An object of the present invention to provide a medical gripping device which alone can close a large tear of an in vivo tissue.

Means for Solving the Problems

A medical gripping device according to the present invention includes a fixed clip, a pair of movable clips made from an elastic material and provided to face the fixed clip, the movable clips having lower ends fixed to the fixed clip and the other ends opened, and a control mechanism which shifts from each other a timing at which a gripping target is gripped between one of the movable clips and the fixed clip and a timing at which the gripping target is gripped between the other movable clip and the fixed clip.

Further, the two movable clips are urged to be opened with the fixed clip therebetween, the two movable clips have protrusion portions protruding away from the fixed clip respectively, the two protrusion portions are provided to be shifted from each other in a longitudinal direction of the fixed clip, the control mechanism is a clip controller provided to surround the two movable clips, and the clip controller acts to draw the two movable clips toward the fixed clip as the clip controller moves from bases of the movable clips toward distal end portions of the movable clips, so that the distal end portions of the movable clips abut against the fixed clip to grip the gripping target at positions where vicinities of the protrusion portions of the movable clips abut against an inner wall of the clip controller respectively.

Further, a lower end portion of the fixed clip is configured to be separable from a flexible operation shaft.

Further, a support portion which supports the fixed clip is provided between the fixed clip and the flexible operation shaft, and a lower end of the support portion is linked with the flexible operation shaft so as to form a separation portion between the support portion and the fixed clip.

Further, slits or notches are formed in a distal end portion of the fixed clip so that the distal end portions of the movable clips directly face each other therethrough.

Further, an engagement portion which engages with the clip controller is provided between the protrusion portion of each movable clip and the distal end portion of the same movable clip.

Further, an operation portion is provided on a proximal side of the flexible operation shaft, the flexible operation shaft is covered with an inner cylinder, the inner cylinder is slidably covered with an outer cylinder, a distal end of the outer cylinder is opened, and a distal end portion of the outer cylinder is formed into an accommodation portion for the movable clips.

Effect of the Invention

According to the invention, the pair of movable clips abut against the fixed clip at timings shifted from each other, so that a large tear or the like in an in vivo tissue of a body is closed. In addition, the movable clips are fixed to the opposite sides of the fixed clip respectively so that the aforementioned treatment is achieved with the gripping device alone. Accordingly, the operational performance is extremely high.

Due to the slits or the notches provided in the distal end portion of the fixed clip, the in vivo tissue can be closed directly.

Since the engagement portions for engagement with the clip controller are provided in the movable clips, the clip controller can be prevented from dropping out from the distal end portions of the movable clips.

Since the fixed clip can be separated from the flexible operation shaft, only the distal end portion thereof can be left in the body while the other portions of the device can be removed from the body.

The movable clips can be protected by the outer cylinder when the device is not in use. As exemplified above, various effects can be provided.

MODE FOR CARRYING OUT THE INVENTION

Embodiments of the present invention will be described below with reference to the drawings.

Figure 1:
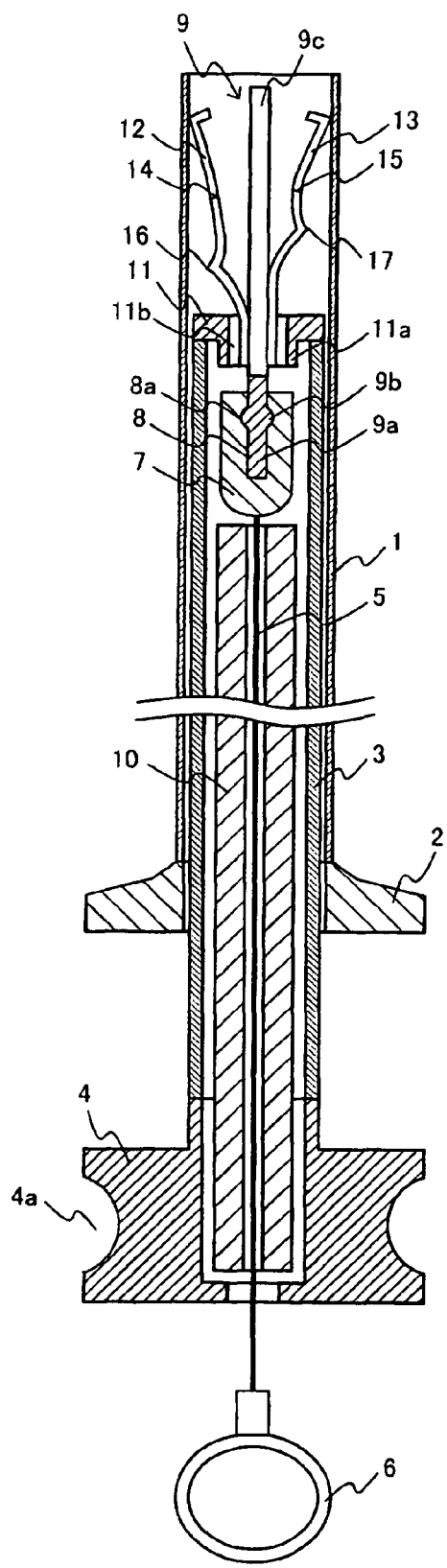
FIG. 1 is a sectional front view of a medical gripping device according to an embodiment of the invention.

As shown in FIG. 1, a flexible pipe 1 serving as an outer cylinder is provided. This flexible pipe 1 is a cylindrical body made of soft resin or the like, and having an outer diameter of about 3 mm and a length of about 150 to 180 cm. The opposite end portions of the flexible pipe 1 are opened, and an operator 2 is attached to a proximal side of the flexible pipe 1 integrally. This operator 2 is made of hard resin.

A flexible pipe 3 serving as an inner cylinder is inserted into the flexible pipe 1. The flexible pipe 3 is freely insertable into the flexible pipe 1. The opposite ends of the flexible pipe 3 are opened, and a proximal-side operator 4 made from hard resin is fixedly attached to a proximal side of the flexible pipe 3. A recess portion 4a is provided to receive a finger of a hand.

A flexible operation shaft 5 is inserted through inside the flexible pipe 3. This flexible operation shaft 5 consists of a stainless steel wire, a composite wire or the like.

A proximal side of the flexible operation shaft 5 comes out from the proximal-side operator 4, and an operation ring 6 serving as an operation portion is attached to a proximal end of the flexible operation shaft 5. One end of a support portion 7 made of resin is fixedly attached to a distal end portion of the flexible operation shaft 5. A recess portion 8 is formed to extend from a distal end toward an inside of this support portion 7. A columnar body 9a arranged under a fixed clip 9 is inserted into the recess portion 8. A protrusion portion 9b is formed in the columnar body 9a, and the protrusion portion 9b is fitted into a recess portion 8a formed in an inner wall of the recess portion 8.

The recess portion 8 and the columnar body 9a are linked in such a manner that the protrusion portion 9b can be released from the recess portion 8a when both portions are pulled a little strongly to thereby separate both the recess portion 8 and the columnar body 9a from each other. To attain such an operation, it is necessary to make the support portion 7 with a slightly soft resin, and to make the recess portion 8a to be shallow enough to allow the columnar body 9a to drop out from the support portion 7 when a certain force is applied thereto.

The configuration of this portion is not limited to that of the embodiment, but various configurations may be adapted. For example, a recess portion or a cut groove may be provided on the fixed clip 9 side. A recess portion may be formed in the wall surface of the fixed clip 9, and a protrusion portion provided in the distal end portion of the flexible operation shaft 5 may be fitted into the recess portion.

Figure 3A:
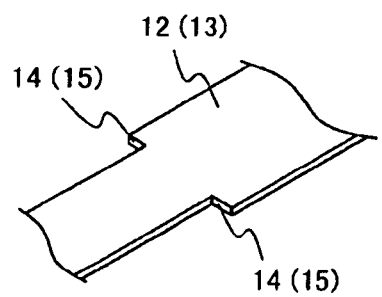
FIGS. 3A and 3B are perspective views showing portions of the same device respectively.
Figure 3B:
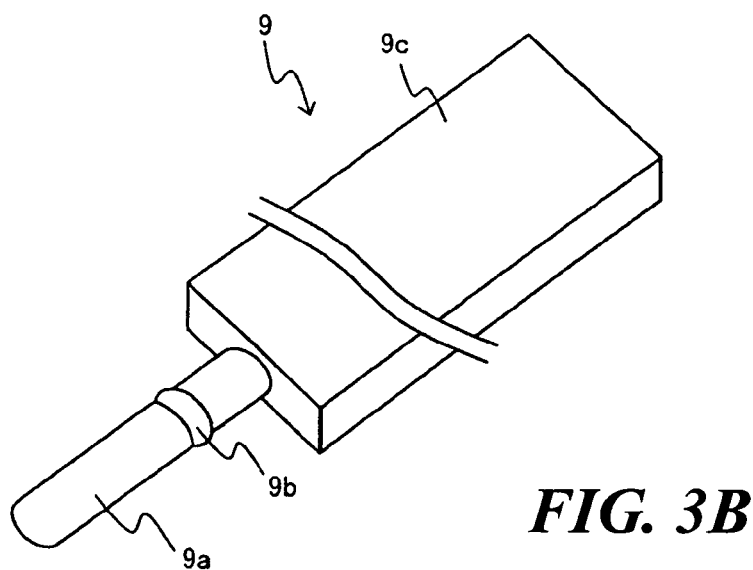

The fixed clip 9 has a shape shown in FIG. 3B. The fixed clip 9 as a whole has a plate-like body with the columnar body 9a formed integrally in its lower end portion. Metal such as stainless steel or titanium is suitable for the material of the fixed clip 9. Resin may be used if possible. Although it is called as the "fixed clip", the fixed clip 9 may be completely non-bendable, but may be slightly bendable.

A flexible pipe 10 is provided between the flexible operation shaft 5 and the inner wall of the flexible pipe 3 serving as the inner cylinder. This flexible pipe 10 serves to prevent the flexible operation shaft 5 from being cured accidentally inside the flexible pipe 3.

A ring-like clip controller 11 is provided inside the flexible pipe 1 and in contact with the distal end portion of the flexible pipe 3. The fixed clip 9 and movable clips 12 and 13 run through a central hole 11b of the clip controller 11. The clip controller 11 is made of hard resin. A small-diameter portion 11a at a lower end of the clip controller 11 is put into the flexible pipe 3.

The clip controller 11 may be shaped like a circular ring, but may have any shape such as an elliptic shape or a rectangular shape. The clip controller 11 does not have to be a complete ring, but may be slightly discontinuous. Essentially, it works well as long as the clip controller 11 has portions which abut against the movable clips 12 and 13 so as to control the movable clips 12 and 13, and which prevent the clip controller 11 from dropping out from the movable clips 12 and 13 when the clip controller 11 is finally holding the movable clips 12 and 13. The clip controller 11 may be generically referred to as ring-like body.

Figure 2:
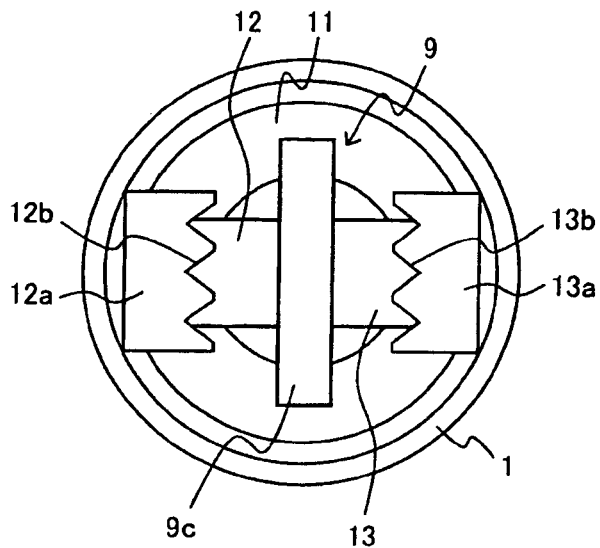
FIG. 2 is a top view of the same device according to the same embodiment.

The movable clips 12 and 13 are provided to sandwich the fixed clip 9 therebetween. Base portions of the movable clips 12 and 13 are fixedly attached around the base of a flat plate portion 9c of the fixed clip 9 by welding. As shown in FIG. 2, the distal end of each movable clip 12, 13 is bent into an L-shape, and irregularities having sharp edges are formed at the distal end of the movable clip 12, 13 so as to grip an in vivo tissue easily. The reference numeral 12a, 13a represents the L-shaped portion, and 12b, 13b represents the irregular portion.

Each movable clip 12, 13 is narrowed halfway and provided with step portions 14, 15 symmetrically on the opposite sides as shown in FIG. 3A. The clip controller 11 engages with the step portions 14, 15. The step portions may be replaced by protrusion pieces with which the clip controller 11 can engage. That is, an engagement portion or engagement portions is required. Although it is preferable that such engagement portions are provided in both the movable clips 12 and 13, an engagement portion may be provided in only one of the movable clips 12 and 13.

Figure 4:
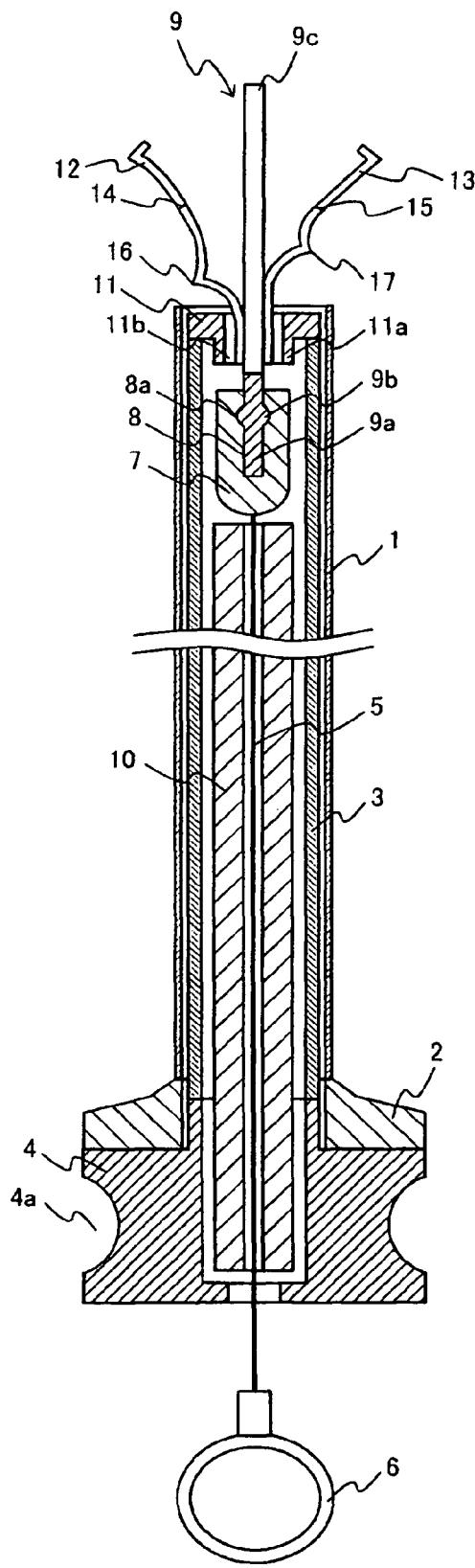
FIG. 4 is a sectional front view of the same device for explaining the operation of the device.

The movable clips 12 and 13 are made of an elastic material such as stainless steel or titanium. Both the movable clips 12 and 13 are urged to be opened with respect to the fixed clip 9. Accordingly, a considerable distance is typically secured between the distal end of the fixed clip 9 and the distal end of each movable clip 12, 13 as shown in FIG. 4.

A protrusion portion 16, 17 hanging outside is formed on the base side of each movable clip 12, 13 with respect to the step portion 14, 15 thereof. The protrusion portions 16 and 17 are not provided symmetrically with respect to the fixed clip 9, but are provided to be displaced slightly from each other in the longitudinal direction of the fixed clip 9. The degree of the displacement is decided in the following manner. That is, the curvature of the movable clip 13 and the position of the protrusion portion 17 are designed such that the inner wall of the clip controller 11 does still not abut against the movable clip 13 when the inner wall of the clip controller 11 abuts against the protrusion portion 16 of the movable clip 12. The distal ends of the protrusion portions 16 and 17 do not have to be sharpened as shown in FIG. 1, but may be rounded.

In addition, the distal end portions of the movable clips 12 and 13 are designed to abut against the fixed clip 9 to thereby grip a gripping target at positions where the vicinities of the protrusion portions 16 and 17 of the movable clips 12 and 13 abut against the inner wall of the clip controller 11 respectively.

Next, the operation of the medical gripping device will be described.

First, as shown in FIG. 1, by the proximal-side operator 4 held in a hand, the operator 2 is moved to leave the proximal-side operator 4. The outer cylinder 1 moves together with the operator 2 to surround the fixed clip 9 and the movable clips 12 and 13. This is a storage state in which the device is not in use.

In use, the operator 2 is pulled down to the proximal-side operator 4 as shown in FIG. 4. Then, the fixed clip 9 and the movable clips 12 and 13 are exposed from the distal end of the outer cylinder 1. Since the movable clips 12 and 13 are urged to leave the fixed clip 9, the movable clips 12 and 13 are opened as shown in FIG. 4.

Figure 5:
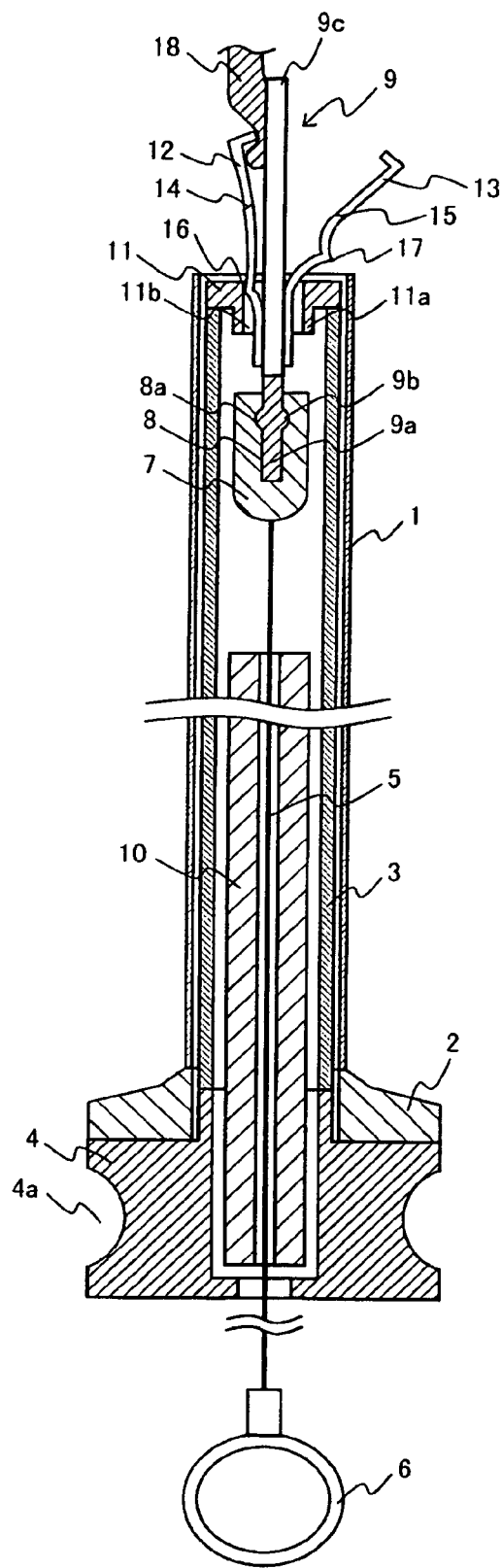
FIG. 5 is a sectional front view of the same device for explaining the operation of the device.

Next, as shown in FIG. 5, the operation ring 6 is pulled while the proximal-side operator 4 is fixed. Then, the operation shaft 5 is also pulled, and the support portion 7 attached to the operation shaft 5 also moves downward. In accordance with this, the fixed clip 9 and the movable clips 12 and 13 also move downward. As the operation proceeds, the pulling degree of the operation ring 6 is adjusted.

First, the outer side of the movable clip 12 abuts against the edge of the central hole 11b of the clip controller 11 so as to narrow the distance between the fixed clip 9 and the movable clip 12. On this occasion, the fixed clip 9 and the distal end of the movable clip 12 grips one side portion 18 of a large tear in an in vivo tissue. When the operation ring 6 is further pulled, the protrusion portion 16 of the movable clip 12 enters the central hole 11b of the clip controller 11. In this state, the one side portion 18 of the tear in the in vivo tissue is gripped tightly between the distal end portion of the fixed clip 9 and the distal end portion of the movable clip 12.

Figure 6:
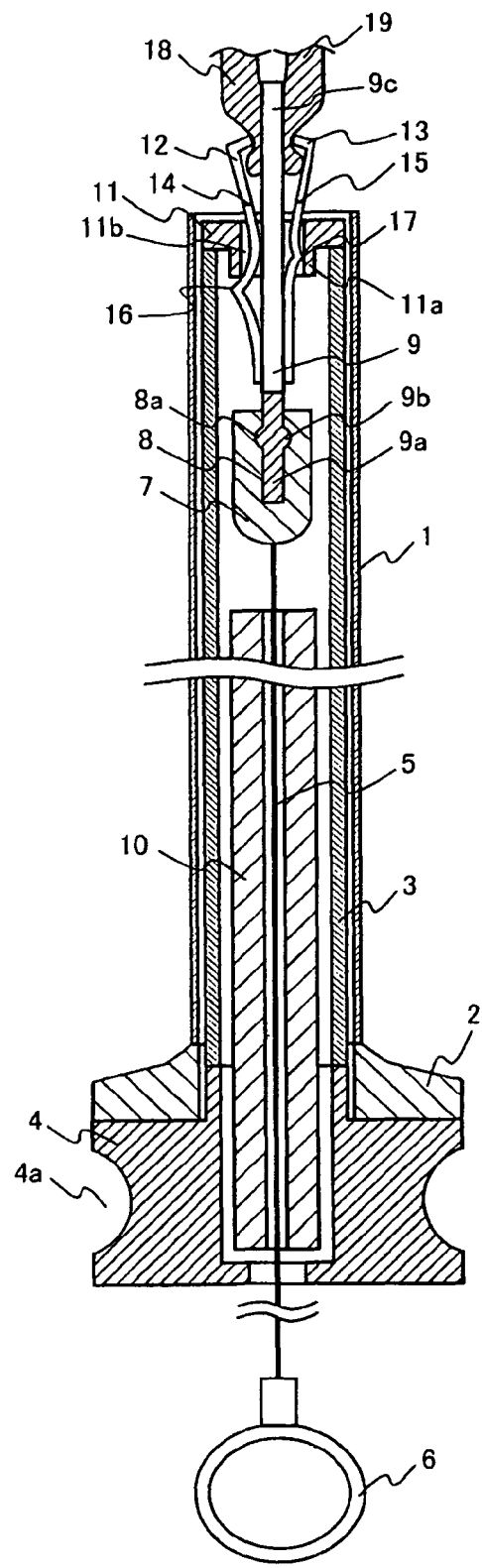
FIG. 6 is a sectional front view of the same device for explaining the operation of the device.

Next, as shown in FIG. 6, when the operation ring 6 is further pulled, the outer side of the movable clip 13 abuts against the edge of the central hole 11b of the clip controller 11. When the operation ring 6 is further pulled, the distance between the fixed clip 9 and the movable clip 13 is narrowed. On this occasion, the fixed clip 9 and the distal end portion of the movable clip 13 grips the other side portion 19 of the tear in the in vivo tissue. When the operation ring 6 is further pulled such that the protrusion portion 17 of the movable clip 13 is positioned in the central hole 11b of the clip controller 11, the other side portion 19 of the tear in the in vivo tissue can be gripped tightly between the fixed clip 9 and the distal end portion of the movable clip 13.

On this occasion, while the protrusion portion 16 of the movable clip 12 has dropped out from the lower end of the central hole 11b of the clip controller 11, the outer side of the movable clip 12 abuts against the opening edge of the central hole 11b of the clip controller 11 so as to tightly grip the side portion 18 of the in vivo tissue. As shown in FIG. 6, the distal end portion of the clip controller 11 engages with the step portions 14 and 15 of the two movable clips 12 and 13 so that the clip controller 11 is prevented from further moving upward.

Figure 7:
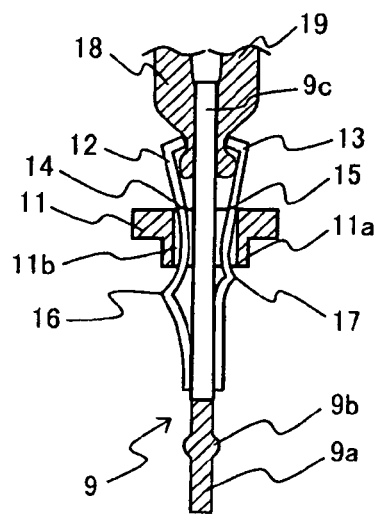
FIG. 7 is a sectional front view of a portion of the same device for explaining the operation of the device.

In this manner, the movable clips 12 and 13 can be brought into contact with the fixed clip 9 at timings shifted from each other. Thus, the large tear of the in vivo tissue can be closed. When the operation ring 6 is further pulled in this state, a slightly strong force is applied to the support portion 7 so as to allow the columnar body 9a of the fixed clip 9 to drop out from the support portion 7, as shown in FIG. 7. The portion shown in FIG. 7 is left in the body, while other portions are extracted outside the body.

Figure 8A:
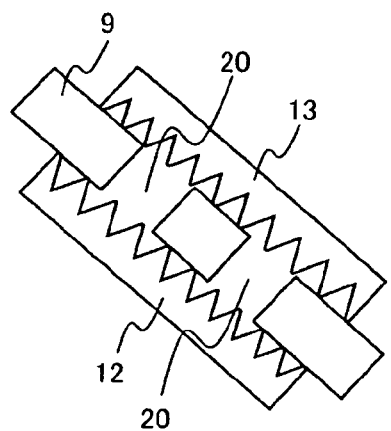
FIGS. 8A and 8B are views showing another example of portions of the same device.
Figure 8B:
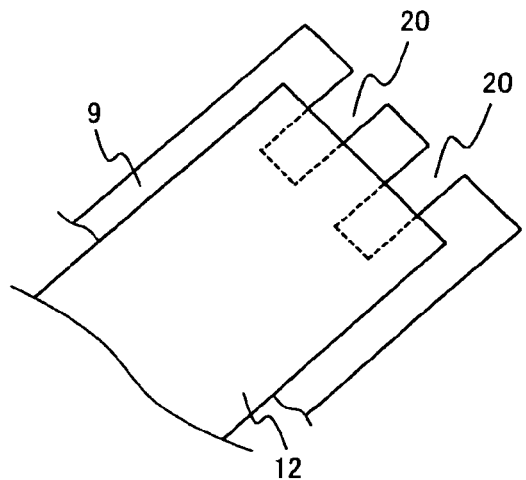

When plural slits 20 are provided in the distal end portion of the fixed clip 9 so as to provide a portion where irregular portions 12b and 13b of the movable clips 12 and 13 can engage with each other directly (without the fixed clip 9 therebetween) as shown in FIGS. 8A and 8B, the opposite side portions 18 and 19 of the tear in the in vivo tissue can be closed directly. Also in this case, it is necessary to provide portions for gripping the side portions 18 and 19 of the tear in the in vivo tissue between the fixed clip 9 and each of the movable clips 12 and 13. The slits 20 may be replaced by notches provided in a one-side portion of the fixed clip 9.

When the large tear in the in vivo tissue is closed as shown in FIG. 7, the opposite side portions of the tear are close to each other. After that, plural background-art devices may be used to further grip the tear directly at several places.

A user may want to turn the directions of the fixed clip 9 and the movable clips 12 and 13 for use due to some longitudinal direction of a large tear in an in vivo tissue. In this case, the operator 2 and the proximal-side operator 4 may be held to rotate the fixed clip 9 and the movable clips 12 and 13. The rotation will be hardly transmitted to their distal end portions when the flexible pipes 1 and 3 are made of resin only. Therefore, flexible pipes in which coil tubes made of metal wires are covered with resin will be used to realize the smooth transmission of rotation toward the distal end portions. Such flexible pipes are also used in background-art products.

Figure 9:
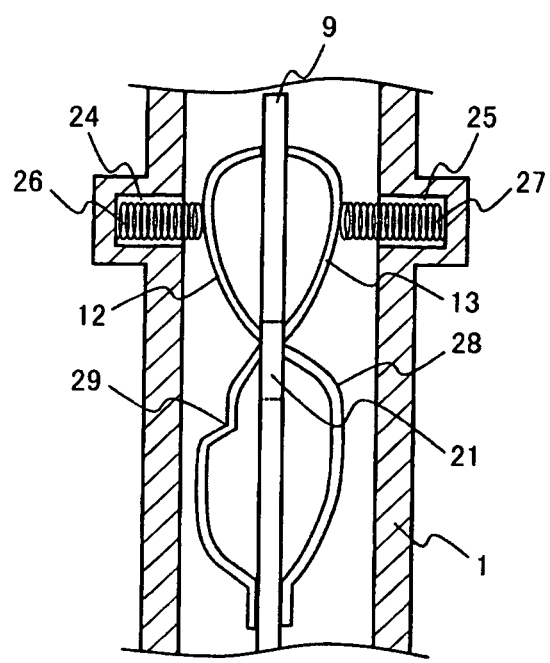
FIG. 9 is a sectional front view of a main portion of a medical gripping device according to another embodiment of the invention.

Next, another embodiment will be described with reference to FIGS. 9 to 13. First, a basic configuration will be described with reference to FIG. 9. Movable clips 12 and 13 and other parts below a clip controller 11 in FIG. 9 are the same as those in FIG. 1, and thus, description will be omitted. The same reference numerals will be applied to parts whose names are the same as those in FIG. 1.

Figure 10A:
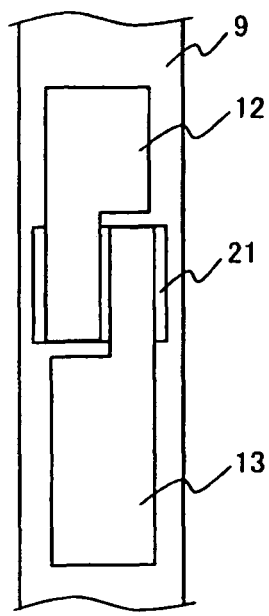
FIGS. 10A and 10B are plan views showing portions of the same device respectively.
Figure 10B:
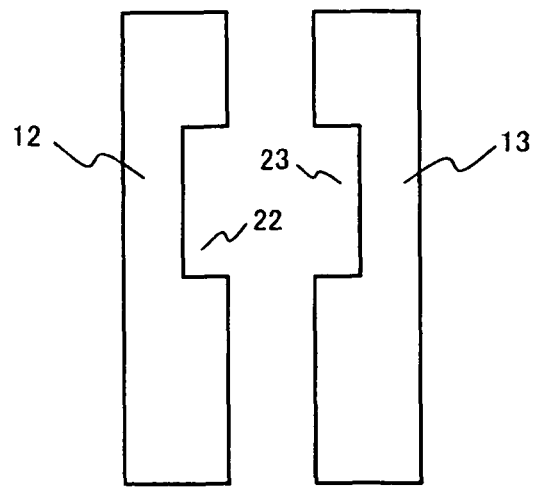

Although FIG. 1 shows the embodiment in which the movable clips 12 and 13 are urged to be separated from each other with respect to the fixed clip 9, FIG. 9 shows the embodiment in which the movable clips 12 and 13 are urged to be closed with respect to the fixed clip 9. As shown in FIG. 10A, a through hole 21 is provided in the fixed clip 9. The movable clips 12 and 13 are inserted into the through hole 21. In order to insert the two movable clips 12 and 13 into the through hole 21, notches 22 and 23 are provided in the movable clips 12 and 13 as shown in FIG. 10B.

As shown in FIG. 9, the lower end portions of the movable clips 12 and 13 are fixedly attached to the lower portion of the fixed clip 9 by welding in advance. The movable clips 12 and 13 cross each other in the through hole 21. The distal end portions of the movable clips 12 and 13 abut against the fixed clip 9. The movable clips 12 and 13 are made from elastic bodies of stainless steel or the like. Irregular portions shown in FIG. 2 are formed in the distal end portions of the movable chips 12 and 13.

The movable clips 12 and 13 are shaped asymmetrically on the proximal side. That is, a front of the proximal-side portion of the movable clip 13 rises (as a high portion 28), and a step portion 29 which is low is provided in the movable clip 12 at a portion opposed to the high portion 28.

The distal end portion of the outer cylinder 1 is formed to be thick, and a pair of pockets 24 and 25 are formed to face each other. Springs 26 and 27 are fitted into the pockets 24 and 25.

Next, the operation of this device will be described.

As shown in FIG. 9, in a storage state, the fixed clip 9 and the movable clips 12 and 13 are covered with the outer cylinder 1. The springs 26 and 27 abut against the movable clips 12 and 13. The movable clips 12 and 13 are pressed onto the fixed clip 9 not by the forces of the springs 26 and 27, but by being originally urged toward the fixed clip 9.

Figure 11:
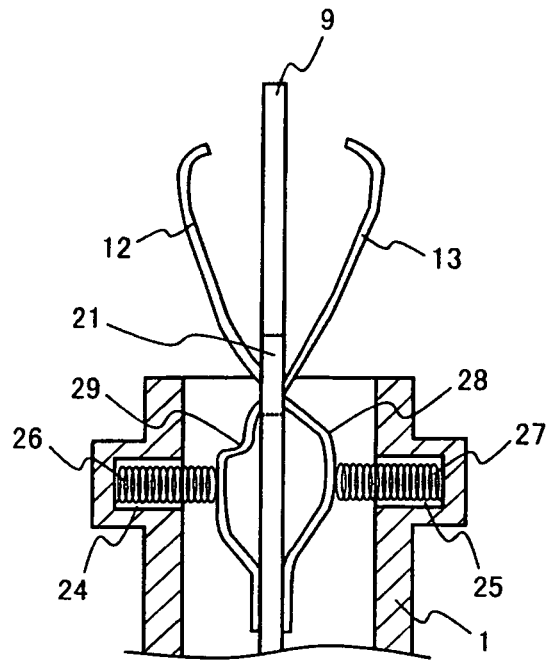
FIG. 11 is a sectional front view of a main portion of the same device for explaining the operation of the device.
Figure 12:
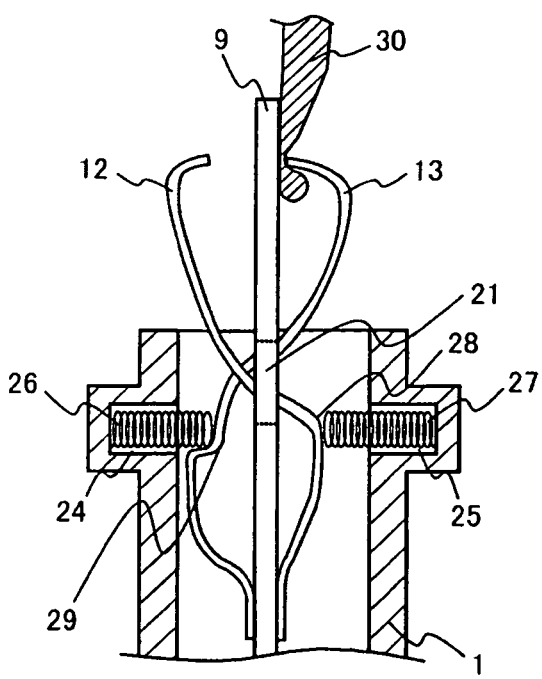
FIG. 12 is a sectional front view of the main portion of the same device for explaining the operation of the device.

The outer cylinder 1 is pulled down to urge the proximal-side portions of the movable clips 12 and 13 by the springs 26 and 27 as shown in FIG. 11. Then, the distal end portions of the movable clips 12 and 13 are opened. This is because the portion where the movable clips 12 and 13 cross each other moves downward in the through hole 21 at the same time as the proximal-side portions of the movable clips 12 and 13 are pushed.

In this state, the fixed clip 9 is moved downward. One side portion of a tear in an in vivo tissue is positioned between the fixed clip 9 and the movable clip 13, and the springs 26 and 27 are positioned in the step portion 29 and the high portion 28. Then, the movable clip 12 is kept opened while the movable clip 13 is closed to grip the one side portion 30 of the tear in the in vivo tissue with the fixed clip 9.

Figure 13:
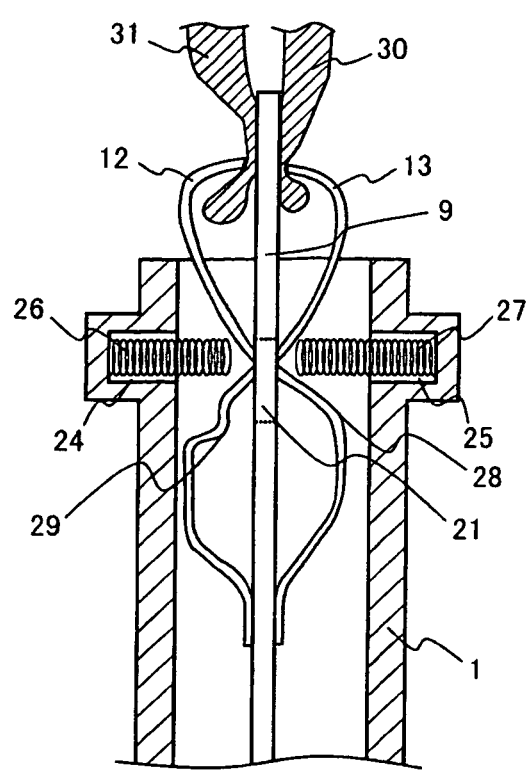
FIG. 13 is a sectional front view of the main portion of the same device for explaining the operation of the device.

Next, the other side portion of the tear in the in vivo tissue is positioned between the fixed clip 9 and the movable clip 12. When the fixed clip 9 is further pulled down, the movable clip 12 grips the other side portion 31 of the tear in the in vivo tissue with the fixed clip 9 as shown in FIG. 13.

When the operation ring 6 shown in FIG. 1 is pulled strongly, the fixed clip 9 drops out from the support portion 7. If the outer cylinder 1 is merely pulled in this state, the springs 26 and 27 ride on the proximal-side portions of the movable clips 12 and 13 again to open the movable clips 12 and 13. Thus, the outer cylinder is suitably rotated with a small amount to remove the outer cylinder 1 in the position where the springs 26 and 27 cannot ride on the movable clips 12 and 13.

For example, the structure of FIGS. 8A and 8B is also applicable to this embodiment.

INDUSTRIAL APPLICABILITY

The present invention is usefully applicable to treatment of a large tear in an in vivo tissue.

DESCRIPTION OF REFERENCE NUMERALS AND SIGNS

1: flexible pipe
2: operator
3: flexible pipe
4: proximal-side operator
5: flexible operation shaft
6: operation ring
7: support portion
8, 8a: recess portion
9: fixed clip
9a: columnar body
9b: protrusion portion
9c: flat plate portion
10: flexible pipe
11: clip controller
11a: small-diameter portion
11b: central hole
12, 13: movable clip
14, 15: step portion
16, 17: protrusion portion
18, 19: in vivo tissue
20: slit
21: through hole
22, 23: notch
24, 25: pocket
26, 27: spring
28: high portion
29: step portion
30, 31: in vivo tissue

The invention claimed is:

1. A medical gripping device, comprising:
a fixed clip;
a pair of movable clips comprising an elastic material and provided to face the fixed clip, the movable clips including lower ends fixed to the fixed clip and upper ends opened; and
a control mechanism which shifts from each other a timing at which a gripping target is gripped between one of the movable clips and the fixed clip and a timing at which the gripping target is gripped between another one of the movable clips and the fixed clip,
wherein the control mechanism is configured to move the movable clips toward the fixed clip as the control mechanism moves in a direction from bases of the movable clips toward distal end portions of the movable clips,
wherein an operation portion of the movable clips is provided on a proximal side of a flexible operation shaft,
wherein the flexible operation shaft is covered with an inner cylinder, and
wherein the inner cylinder is slidably covered with an outer cylinder.

2. The device of claim 1, wherein the movable clips are urged to be opened with the fixed clip therebetween,
wherein the movable clips include protrusion portions protruding away from the fixed clip respectively,
wherein the protrusion portions are provided to be shifted from each other in a longitudinal direction of the fixed clip,
wherein the control mechanism comprises a clip controller provided to surround the movable clips, and
wherein the clip controller acts to draw the movable clips toward the fixed clip as the clip controller moves from the bases of the movable clips toward the distal end portions of the movable clips, so that the distal end portions of the movable clips abut against the fixed clip to grip the gripping target at positions where vicinities of the protrusion portions of the movable clips abut against an inner wall of the clip controller respectively.

3. The device of claim 2, wherein an engagement portion which engages with the clip controller is provided between the protrusion portion of each of the movable clips and the distal end portion of said each of the movable clips.

4. The device of claim 2,
wherein a distal end of the outer cylinder is opened, and
wherein a distal end portion of the outer cylinder is formed into an accommodation portion for the movable clips.

5. The device of claim 1, wherein a lower end portion of the fixed clip is configured to be separable from the flexible operation shaft.

6. The device of claim 5, wherein a support portion which supports the fixed clip is provided between the fixed clip and the flexible operation shaft, and
wherein a lower end of the support portion is linked with the flexible operation shaft so as to form a separation portion between the support portion and the fixed clip.

7. The device of claim 1, wherein slits or notches are formed in a distal end portion of the fixed clip so that the distal end portions of the movable clips directly face each other therethrough.

8. The device of claim 1, wherein the control mechanism comprises a clip controller provided to surround the movable clips.

9. The device of claim 8, wherein the clip controller draws the movable clips toward the fixed clip as the clip controller moves from the bases of the movable clips toward the distal end portions of the movable clips, such that the distal end portions of the movable clips abut against the fixed clip to grip the gripping target at positions where vicinities of protrusion portions of the movable clips abut against an inner wall of the clip controller respectively.

10. The device of claim 9, wherein the movable clips include protrusion portions protruding away from the fixed clip respectively.

11. The device of claim 10, wherein the protrusion portions are provided to be shifted from each other in a longitudinal direction of the fixed clip.

12. The device of claim 1, wherein the control mechanism comprises a clip controller provided to surround the movable clips, and
wherein an engagement portion which engages with the clip controller is provided between the protrusion portion of each of the movable clips and the distal end portion of said each of the movable clips.

13. The device of claim 1, wherein a distal end of the outer cylinder is opened, and
wherein a distal end portion of the outer cylinder is formed into an accommodation portion for the movable clips.

14. A medical gripping device, comprising:
a fixed clip;
a pair of movable clips comprising an elastic material and provided to face the fixed clip, the movable clips including lower ends fixed to the fixed clip and upper ends opened; and
a control mechanism which shifts from each other a timing at which a gripping target is gripped between one of the movable clips and the fixed clip and a timing at which the gripping target is gripped between another one of the movable clips and the fixed clip,
wherein the movable clips are urged to be opened with the fixed clip therebetween,
wherein the movable clips include protrusion portions protruding away from the fixed clip respectively,
wherein the protrusion portions are provided to be shifted from each other in a longitudinal direction of the fixed clip,
wherein the control mechanism comprises a clip controller provided to surround the movable clips,
wherein the clip controller acts to draw the movable clips toward the fixed clip as the clip controller moves from bases of the movable clips toward distal end portions of the movable clips, so that the distal end portions of the movable clips abut against the fixed clip to grip the gripping target at positions where vicinities of the protrusion portions of the movable clips abut against an inner wall of the clip controller respectively,
wherein an operation portion of the movable clips is provided on a proximal side of a flexible operation shaft,
wherein the flexible operation shaft is covered with an inner cylinder, and
wherein the inner cylinder is slidably covered with an outer cylinder.

* * * * *